(12) United States Patent
Muratidi (10) Patent No.: US 12,133,774 B2
(45) Date of Patent: Nov. 5, 2024

(54) SUPPORT ARM ARTICULATION APPARATUS AND SUPPORT SYSTEM FOR A MEDICAL DEVICE

(71) Applicant: ONDAL MEDICAL SYSTEMS GMBH, Hünfeld (DE)

(72) Inventor: Georg Muratidi, Oberaula (DE)

(73) Assignee: ONDAL MEDICAL SYSTEMS GMBH, Hünfeld (DE)

(*) Notice: Subject to any disclaimer, the term of this patent is extended or adjusted under 35 U.S.C. 154(b) by 3 days.

(21) Appl. No.: 17/760,130

(22) PCT Filed: Feb. 5, 2021

(86) PCT No.: PCT/EP2021/052846
§ 371 (c)(1),
(2) Date: Aug. 4, 2022

(87) PCT Pub. No.: WO2021/156463
PCT Pub. Date: Aug. 12, 2021

(65) Prior Publication Data
US 2023/0067339 A1     Mar. 2, 2023

(30) Foreign Application Priority Data
Feb. 6, 2020  (EP) .................................... 20155980

(51) Int. Cl.
*A61B 90/50*     (2016.01)
*F16M 13/02*    (2006.01)
*A61B 90/00*     (2016.01)

(52) U.S. Cl.
CPC ........... *A61B 90/50* (2016.02); *F16M 13/022* (2013.01); *A61B 2090/064* (2016.02);
(Continued)

(58) Field of Classification Search
CPC ............. A61B 90/50; A61B 2090/508; F16M 13/022; F16M 2200/047; F16M 2200/068
See application file for complete search history.

(56) References Cited

U.S. PATENT DOCUMENTS 5,340,072 A     8/1994   Halbirt
7,837,674 B2 *  11/2010  Cooper .................. A61B 34/37
                                                                  606/1
(Continued)

FOREIGN PATENT DOCUMENTS

JP   2006230691 A   9/2006
WO   2011/102630 A2  8/2011

OTHER PUBLICATIONS

International Search Report issued in International Application No. PCT/EP2021/052846 dated May 25, 2021.

*Primary Examiner* — Monica E Millner
(74) *Attorney, Agent, or Firm* — MEDLER FERRO WOODHOUSE & MILLS PLLC (57)     ABSTRACT

The invention relates to a support arm articulation device (50) for movably holding a medical device, comprising a first and a second fastening element (52, 54), which are connected to each other in a pivotable way by means of a spring arm (56), wherein the spring arm (56) comprises a supporting arm (58) and a lever arm (60), which are mounted in a pivotable way on the first fastening element (52) with an associated supporting arm pivot axis (64) and lever arm pivot axis (66), wherein the two pivot axes (64, 66) are spaced apart from one another, wherein the supporting arm (58) is mounted on the second fastening element (44) in a pivotable way, and the lever arm (60) is mounted on the supporting arm (58) by means of a spring device (78) such that a weight of the held medical device is supported in different pivot positions, wherein the spring device (78) comprises an adjustment device, by means of which a
(Continued)

position of the mounting (68, 70) of the lever arm (60) on the supporting arm (58) is adjustable along a longitudinal extension of the supporting arm (58). Further, the invention relates to a support arm system and a method for operating a support arm articulation device.

20 Claims, 6 Drawing Sheets

(52) U.S. Cl.
CPC .. *A61B 2090/508* (2016.02); *F16M 2200/047* (2013.01); *F16M 2200/068* (2013.01)

(56) References Cited

U.S. PATENT DOCUMENTS

| | | | | |
|---|---|---|---|---|
| 8,585,001 | B2 * | 11/2013 | Huang | F16M 11/2092 |
| | | | | 248/371 |
| 8,931,748 | B2 * | 1/2015 | Bowman | F16M 13/022 |
| | | | | 248/917 |
| 10,285,772 | B2 * | 5/2019 | Oginski | A61G 12/002 |
| 11,118,729 | B2 * | 9/2021 | Zebarjad | F16M 13/022 |
| 11,576,734 | B2 * | 2/2023 | Schena | A61B 90/50 |
| 2007/0080275 | A1 * | 4/2007 | Stachowski | F16M 11/2014 |
| | | | | 248/323 |
| 2007/0156122 | A1 | 7/2007 | Cooper | |
| 2009/0322001 | A1 | 12/2009 | Luke et al. | |
| 2011/0023285 | A1 * | 2/2011 | Cooper | A61B 34/71 |
| | | | | 29/428 |
| 2011/0315843 | A1 * | 12/2011 | Hung | F16M 13/022 |
| | | | | 248/278.1 |
| 2017/0340408 | A1 | 11/2017 | Oginski et al. | |
| 2018/0200008 | A1 * | 7/2018 | Cooper | A61B 34/30 |
| 2018/0310903 | A1 * | 11/2018 | Rowland | F16M 11/2035 |

* cited by examiner

Fig.1
(State of the Art)

Fig.2
(State of the Art)

SUPPORT ARM ARTICULATION APPARATUS AND SUPPORT SYSTEM FOR A MEDICAL DEVICE

The present invention relates to a support arm articulation device for a support system for holding at least one medical device, and a support system for a medical device.

Support arm systems are used in surgery rooms, for example, to hold a medical equipment or device in a way that the position thereof may be altered. Hereto, a support arm may be movably anchored by means of a mounting assembly on a ceiling, a wall, or a floor, for example. A fastening to a frame including roles is also possible. A support system comprising at least one support arm may also be denoted as a support arm system, and a support system which is configured for holding medical devices may also be denoted as a medical support system. In general, support systems comprise at least one axis of movement, thus the held medical equipment, which may also be denoted as medical engineering equipment and may for example include a surgery lamp, a monitor, examination equipment, one or more injectors, a surgical kit or dental drill sets, may be moved according to the respective requirements. The mounting which enables the movement may also be denoted as articulation device or support arm articulation device, which may also comprise a support arm. Thus, the medical equipment may be brought into a comfortable and secure position for performing the respective medical procedures and monitoring. The local displacement of medical equipment is vital for many medical procedures in order to facilitate or generally enable the work of medical staff.

However, by pivoting a support arm, a lever arm may be changed regarding the mounting thereof. In particular during pivoting of the support arm around an essentially horizontal axis, whereby the height of the medical device held thereon may be changed, a lever arm of the weight force of the medical device is changed regarding the fastening or mounting of the support arm, respectively. However, it is desired that the medical device remains at the position which has been set by pivoting the support arm.

Hereto, often spring balanced support arms or support arm articulation devices are used. Here, two arms are provided spaced from each other, which support each other by means of the spring. By pivoting the spring balanced support arm, the lever arm of the spring force changes correspondingly to the lever arm of the support load, thus the medical device may be held equally well in different positions. Alternatively or in addition, the spring may also be compressed or expanded by the pivot movement, thus a corresponding supporting force may also be changed.

Such a support arm articulation device is for example shown in EP 3 217 939 A1. Here, the distance between a mounting of two arms may be adjusted in order to be able to equally support loads in different sizes or keep them in position. Pivoting the support arm articulation device shown there is performed directly manually, which implies a reachability for the user.

It is also known to use brakes which keep the support arm in its position. However brakes have the disadvantage of being prone to wear. In addition, for brakes a load adjustment may be required.

Further, direct pivoting by using a motor is known, which is arranged on a mounting of a support arm. Hereto however, a large and strong motor may be required. An example for such a technology will be explained in more detail with reference to the figures later.

It is an objective of the present invention to provide an enhanced support arm articulation device, an enhanced support arm system, and an enhanced method for operating a support arm articulation device. In particular, a cost-efficient support of medical devices is to be realized in an exactly settable position in a simple way.

Said objects are achieved according to the invention by means of the subject-matters of the independent claims. Advantageous embodiments and purposeful further developments of the invention are specified in the respective dependent claims, wherein advantageous embodiments of an aspect may be regarded as advantageous embodiments of respective other aspects and vice versa.

A first aspect of the invention relates to a support arm articulation device for a support system for movably holding at least one medical device. Here, the position or posture may be maintained after moving the device, which may also be denoted as a fixation in posture or position.

The support arm articulation device comprises a first and a second fastening element, which are pivotably connected to each other by means of a spring arm in order to pivot relative to one another. Here, the spring arm is also part of the support arm articulation device and enables to move the two fastening elements relative to each other by pivoting at least about one pivot axis, preferably in a pivot plane. One of the two fastening elements, preferably the first fastening element, may be stationary, by being anchored on a wall, for example. The other fastening element may thus preferably be pivoted relative to said anchoring, in particular to alter the height thereof.

The spring arm may comprise a supporting arm and a lever arm, which are mounted in a pivotable way on the first fastening element using an associated supporting arm pivot axis and a lever arm pivot axis. The two pivot axes should be spaced from each other, wherein the pivot axes are preferably arranged parallel to each other. During a pivot movement of the spring arm and/or a pivoting of the two fastening elements relative to each other, respectively, the supporting arm and the lever arm are preferably also pivoted relative to each other. At least one of the two fastening elements is arranged on the spring arm in an articulated way, in particular the first fasting element on both the supporting arm and also the lever arm in an articulated way. Preferably, the other fasting element, in particular the second fastening element, is also mounted on the spring arm in an articulated way, preferably exclusively on the supporting arm.

The supporting arm is preferably mounted on the second fastening element in a pivotable way. In contrast, the lever arm is mounted on the supporting arm by means of a spring device, for example, so that the weight force of the held medical device is supported in different pivot positions. Due to the spring device and the spaced mounting of supporting arm and lever arm, a supporting force of the support arm articulation device may automatically be adapted to the pivot angle or pivot position thereof to equally support the weight force with different lever arm lengths of the weight force. The support arm articulation device is thus self-balancing and/or supports an adjustment of the pivot angle against gravity.

In addition to the weight of the medical device, the self-weight of respective components of the support arm articulation device may thus also be supported or balanced. For example, there also acts a weight force of a non-anchored one of the two fastening elements with different lever arms, whereby different torques may be supported depending on the position of the support arm articulation device.

In the context of this application, the lever arm relates to a component of the support arm articulation device, which may be formed, for example, as a rod, bar, tube, hollow profile, or the like.

Said lever arm thus also supports the medical device to be held. In contrast, lever arms in the context of forces denote the distance of a point of application of force from a pivot joint or pivot point. Such lever arms thus denote a length, whereby by the multiplication thereof with the respective force, the torque acting on the pivot point, which is often also called a moment, may be calculated.

The spring device may comprise an adjustment device by means of which a position of the mounting of the lever arm on the supporting arm is adjustable along a longitudinal extension of the supporting arm. By means of said position adjustment, a position is thus adjusted on which the lever arm acts on the supporting arm. Alternatively or in addition, this way a pivot angle of the lever arm may be set relative to the lever arm pivot axis. In total, said adjustment results in a pivot angle of the support arm articulation device or a relative position of the two fastening elements to each other. Thus, by moving the mounting of the lever arm on the supporting arm and/or moving a point of application of force, thus a pivot angle of the support arm articulation device or the spring arm may be adjusted, respectively.

Preferably, the adjustment device is configured to change a tension state of the spring arm or the spring device by adjusting the mounting of the lever arm on the supporting arm. For example, a spring may be compressed or expanded correspondingly. Preferably, the spring device is configured to store any potential energy released when the support arm articulation device or the medical device held thereon is lowered, and to release it again when the support arm articulation device or the medical device held thereon is raised. For example, when the spring arm is lowered, a spring of the spring device may be compressed by adjusting the mounting of the lever arm on the supporting arm, and when the spring arm is raised, a spring of the spring device may be expanded by adjusting the mounting of the lever arm on the supporting arm. Accordingly, the spring performs a support during lowering, which means that smaller supporting forces have to be applied. When lifting, the spring releases energy stored during lowering, thereby little force is required for lifting. This way a precise setting of the position may easily be performed using less force and a simple mechanism. It may even be necessary to apply a force in addition to the self-weight during moving downwards in order to move the spring arm against the supporting spring force. The support arm articulation device, in particular the spring device, may be configured in a way that approximately the same forces are required for lowering and lifting. Thus an operation and an adjustment of position is possible in an especially intuitive and precise way.

The support arm articulation device thus enables to provide a balanced support arm having an adjustable pivot angle. Due to the adjustment on the spring device it is not required to drag any components for adjusting, and instead a mechanic adjustability may be provided. This enables a substantially more precise and/or faster adjustment, in particular by a reduction or translation, for example, on an adjusting element as a rotary knob.

The adjustment device may also be self-locking, self-blocking and/or arresting. For example, an adjustment screw, like a threaded rod, may be provided which prevents a displacement of the position of the mounting of the lever arm by weight forces of the medical device by means of a thread pitch. Thus the position is precisely held. This may also prevent, or at least reduce at least a swinging after adjustment in an effective way.

In particular, a motorized and/or mechanically adjustable spring arm may thus also be provided in the range of light and medium loads. The design is simple and cost-efficient. The adjustment device may be configured for continuous adjustment, in particular continuous positioning and/or height adjustment. Even in the event of load losses, for example due to dismantling of the medical device, and/or additional loads, for example pressing on control panels of the medical device, the spring arm may remain in position, in particular due to the self-locking mechanism described.

The spring device may, for example, comprise a pre-loaded spring, which, for example, already supports or balances a large part of the acting loads. Thus, an adjustment requires only very little forces, which means, for example, that little operating force and/or only a small motor is/are required. Preferably, the spring is configured as coil spring and/or pressure spring. In addition, the risk of possible collisions in case of an operation error is also reduced, as the operating forces acting then are also small. For example, when used as part of a robotic arm, significantly fewer risk avoidance measures may be required.

The respective fasting elements may be configured to hold a medical device, a support arm and/or an additional support arm articulation device, for example. Preferably, the medical device is fastened to the second fastening element. The medical device may for example be a monitor, an electrocardiogram device, devices for infusions and/or surgeries, part of a drilling kit for dentists, or also a tablet for holding medical tools like scalpels and more. One of the fastening elements may for example be configured for fastening on a wall, ceiling, floor insulation and/or a movable or stationary base unit. The fastening elements may for example comprise a coupling, as for example bolts and/or quick clamps, for fastenings respective components of the support arm system thereon, as for example an additional support arm and/or a medical device. One or both of the fasting elements may also be configured for coupling to a support arm, in particular for a movable coupling. For example, the respective fasting element may comprise a mounting and/or a hinge hereto. This way, the fasting element and thus also the medical device may be aligned in relation to the spring arm and/or the other fasting element, for example by rotation in the vertical or horizontal plane. This results in a flexible and/or modular design.

The lever arm and the supporting arm may be formed as elongated bolts, rod, bar, cylinder, hollow profiles, solid profiles and/or the like. As materials resin or metal are used here, for example. The lever arm and the supporting arm may be configured as one piece or multi pieces. Preferably, the lever arm and the supporting arm are mounted on the respective end on the corresponding supporting arm pivot axis or lever arm pivot axis, that means with the respective end on the first fastening element. The supporting arm is thereof preferably mounted on the second fasting element with its opposite end, in particular in a pivotable or non-rotational way. The lever arm is preferably mounted on the spring device with its opposite end, in particular the adjustment device and/or the supporting arm. Said mounting should be axially adjustable around the pivot adjustment. Preferably, the mounting is here axially supported by the spring device along the longitudinal extension of the supporting arm to be capable to support the respective forces required for adjustment by means of the spring device.

The lever arm is preferably held on the supporting arm by means of the spring device spaced from the second fastening element. The lever arm may be held indirectly on the supporting arm via the spring device or adjustment device, respectively, or it may also be mounted directly on the supporting arm with the adjustment device causing a movement of the mounting and/or the spring device enables a flow of force from the lever arm to the supporting arm, in particular along the axial extension of the supporting arm.

One of the two fastening elements may be displaced locally relative to the other of the two fastening elements by means of the spring arm, in particular in a height-wise or vertical direction. Alternatively or in addition, a local displacement in a transverse or horizontal direction may also be possible by means of the support arm articulation device, in particular by means of the spring arm. Preferably, only one pivot plane, in particular a vertically aligned pivot plane for adjustment in the upward direction, will be balanced by means of the spring arm. For example, the respective fastening elements are arranged at opposite ends of the spring arm, in particular fastened thereto.

A further advantageous embodiment of the support arm articulation device provides that the spring device includes a spring. A spring is a simple element for absorbing or storing and releasing potential energy, which enables a balancing by simple means and/or an adjustment or operating force may be in particular small. For example, a hydraulic or mechanical spring is suitable, in particular a gas pressure spring and/or a coil spring. A mechanical spring is especially cost-efficient and robust. In addition, a spring device may comprise a damping, which for example prevents a sudden bouncing up during relief of strain, for example when removing the medical device. Said damping may be integrated in a hydraulic spring in especially simple way. Preferably, the spring is guided and/or arranged essentially within the supporting arm. This way, the spring is arranged in a way protected against environmental impacts and/or a risk of injury due to an operation error, for example when gripping the spring, may be minimized. Essentially denotes here in particular that the spring may protrude partly from the supporting arm depending on the position of the support arm articulation device or of the spring arm and/or the mounting of the lever arm. Preferably, the spring is completely accommodated in the supporting arm in every position. Hereto, the supporting arm may also comprise a spring tube or may be configured as one.

A further advantageous embodiment of the support arm articulation device provides that the lever arm is mounted on the spring device in a pivotable way, and is mounted with a pivot axis parallel to the lever arm pivot axis by means of which the lever arm is mounted on the first fastening element. The position of the pivot axis may be axially movable along the supporting arm. A respective mounting may also be denoted as a lever mounting. Preferably, the lever arm is mounted within the supporting arm and/or a covering in order to reduce a risk of squeezing and to prevent damages in a reliable way.

A further advantageous embodiment of the support arm articulation device provides that the lever arm is mounted by means of the carriage on the supporting arm along the longitudinal extension thereof, wherein the carriage is preferably guided essentially within the supporting arm. In particular the carriage may be mounted on or in the supporting arm in an axially movable way. In the simplest form, the carriage is adapted to an inner diameter of a tube of the supporting arm and is thus guided. In particular, the lever arm may be pivotably mounted on the carriage. The carriage provides a simple guidance of the lever arm with an axial adjustability and load transfer to or from the spring device.

The arrangement inside also enables a protection of components and people. In particular, it is possible to avoid contamination and thus early wear. The carriage may be part of the adjustment device and is moved axially on the supporting arm during adjustment of the mounting position. Depending on the position, the carriage may protrude partially from the supporting arm or may be completely accommodated therein in any position.

A further advantageous embodiment of the support arm articulation device provides that the adjustment device comprises a threaded rod, thus by the movement thereof the position of the mounting of the lever arm at the supporting arm may be adjusted. Moving the threaded rod may be performed relative to the supporting arm. For example, movement may be caused by turning the threaded rod. Thus, due to turning the threaded rod, the position of the mounting of the lever arm on the supporting arm may be adjusted. The threaded rod enables a translation ratio which may be easily defined by the design, in particular for a reduction. Thus, the adjustment of the support arm articulation device may be performed using little force or little torque. In addition, a threaded rod may also be self-blocking, thus in case of a failure of a drive system, in particular of the motor, and/or a failure of the spring, a support arm or the medical device, respectively, which is held thereon, does not easily drop down. Furthermore, the threaded rod is also able to accept large forces in a reliable way. Preferably, the threaded rod is arranged essentially within the supporting arm, wherein depending on the posture, the threaded rod may project partly from the supporting arm or may be completely accommodated in each position or posture. In a further advantageous embodiment, the threaded rod is also arranged in the supporting arm at least partially or completely. For example, independent of the posture or position, the threaded rod may also be arranged only partially in the supporting arm. However, it may also be completely accommodated in the supporting arm independent of the posture or position, for example. However, the threaded rod may also be arranged in one posture or position completely in the supporting arm, for example, and in another posture or position only in part within the supporting arm. Due to the partly or completely arrangement in the supporting arm, the threaded rod may be protected against damages and dirt. Thus the user is able to prevent an undesired contact with the threaded rod in a complete or partial way.

A further advantageous embodiment of the support arm articulation provides that the threaded rod is mounted on an axially fastened and rotatable nut which is fastened in or on the supporting arm. A rotation of the nut causes an axial adjustment of the position of the threaded rod. The nut may in particular be formed as a spindle nut. Preferably, the threaded rod is fastened on the carriage and/or the lever arm, in particular using one end, preferably the end facing away from the nut. Preferably, the nut may be fastened in the axial position thereof being set along the longitudinal extension of the supporting arm, for example by an abutment element, which is arranged in the corresponding groove of the nut and/or a nut or a seating of the supporting arm. In total, by means of the threaded rod and optionally by means of the nut, a cost-efficient adjustment device may be provided which is almost free of maintenance.

A further advantageous embodiment of the support arm articulation device provides that the adjustment device comprises an adjusting element by means of which the position of the mounting of the lever arm on the supporting arm may be adjusted, wherein the adjusting element is preferably mounted on the supporting arm. The adjusting element may cause a manual displacement of the mounting of the lever arm on the supporting arm, for example, whereby a pivot angle may be correspondingly set manually in a precise way. The adjusting element may thus be configured for a manual operation and/or as a rotary knob. Preferably, the adjusting element is engaged by means of a gear, as for example corresponding bevel gears, engaged with the threaded rods and/or the nut. Preferably, an operation and/or rotational axis of the adjusting element is aligned in a transverse direction, in particular perpendicular to the longitudinal extension of the supporting arm. Respective bevel gears enable to simply predefine a translation ratio and/or to align the operation axis of the adjustment device and the adjusting element in a transverse direction, in particular orthogonal, to each other. In this way, it is possible to configure the support arm articulation device in an especially compact way.

A further advantageous embodiment of the support arm articulation device provides that the adjustment device comprises a motor, by means of which the position of the mounting of the lever arm on the supporting arm may be adjusted, wherein the motor is preferably mounted on the supporting arm. In particular, the motor may be arranged within the supporting arm at least partially or completely, and/or in an axial extension of the supporting arm, thus the device may be formed in a compact and robust way By means of the motor, a drive system for adjusting the support arm articulation device is thus provided. This enables an automation and/or control, in particular, the support arm articulation device may thus simply be used as part of a robotic support arm system. The motor is preferably formed as electric motor. For example, the motor may be configured to rotate the nut and/or the threaded rod. The motor enables an electric control of the pivot angle of the support arm articulation device and/or of the two fastening elements relative to each other. Preferably, the motor is formed as a geared motor.

A further advantageous embodiment of the support arm articulation device provides that the support arm articulation device comprises a sensor device which is configured to detect a force acting on the support arm articulation device and/or a posture of the two fastening elements relative to each other. For example, said detection may also be performed simply by detecting a pivot angle of the supporting arm and/or the lever arm with respect to the supporting arm pivot axis and/or the lever arm pivot axis, for example by means of a protractor. Alternatively or additionally, an accelerometer or image-based detection is appropriate, for example.

In addition, the support arm articulation device may comprise a control device which depending on the detected force acting on the support arm articulation device and/or the detected posture of the support arm articulation device controls the motor in order to maintain the relative posture of the two fastening elements to each other. The detected posture of the support arm articulation device may include or be defined as the relative position or posture of the two fastening elements to each other. Thus, an automatic control for assuming and/or maintaining predefined postures may be implemented. In particular, such a control is possible to maintain the position of the medical device. The support arm articulation device may thus compensate external forces by pressing an actuator of the medical device, for example. This enables to maintain the position in a precise way, so that a corresponding support arm system may also be well used for surgeries which are performed only partially robotically without the risk of an unintentional adjustment caused by an accidental contact with or applying a load on the respective support arms.

A further advantageous embodiment of the support arm articulation device provides that the support arm articulation device includes a parallel guiding element which is mounted pivotably on the first fastening element and the second fastening element at a distance from the supporting arm, respectively, in particular the mounting thereof on the respective fastening element. Preferably, respective mounting axes of the parallel guiding element are parallel to one other and/or to the respective mounting axis of the supporting arm. By means of the parallel guiding element, an orientation of the held medical device may be maintained during pivoting the support arm articulation device or the spring arm. The parallel guiding element is designed, for example, to couple an alignment of the second fastening element to a pivoting movement of the two fastening elements relative to each other. Thus, for example, a monitor may be maintained in a selected orientation, such as a horizontal orientation, even in case the height of the support thereof is adjusted. Preferably, the parallel guiding element is formed as a parallel guiding rod. By means of the parallel guiding element, a coupling of the pivot angle of the first fastening element with the pivot angle of the second fastening element may be provided.

A further advantageous embodiment of the support arm articulation device provides that the support arm articulation device is configured to adjust the supporting force of different weight forces on various held medical devices in different pivot positions, in particular by replacement the spring of the spring device, setting a prestressing force of the spring device and/or adjusting a distance between the lever arm pivot axis and the supporting arm pivot axis on the first fastening element.

Due to the distance between the lever arm pivot axis and the supporting arm pivot axis a lever arm of the supporting force and thus a supporting torque may be set. In addition, the supporting force may be adjusted by means of a spring. The adjustability of the supporting force enables a support arm articulation device which may be leveraged in a particularly variable way. The replacement or provision of springs adapted to the respective payloads enables a particularly cost-effective and robust design.

A further advantageous embodiment of the support arm articulation device provides that the first fastening element and/or the second fastening element is/are designed for fastening on a wall, a ceiling, a floor, a movable and/or a stationary base unit and/or the first fastening element and/or the second fastening element is/are designed for coupling to a support arm, a joint, a further support arm articulation device and/or the medical device(s). Thus a modular design may be enabled. In addition, such a center of gravity of the support arm articulation device may be moved towards a fixed anchoring, whereby the self-weight of the support arm articulation device may be supported or compensated by smaller forces.

A second aspect of the invention relates to a support arm system for movably holding at least one medical device. Said support system comprises a support arm articulation device according to a first aspect of the invention. The support arm articulation device may here also be regarded as a support arm, in particular a spring arm. The support system may comprise one or more support arms and/support arm articulation devices which may be coupled to each other, in particular by means of respective fastening events. Here, for every two support arms and/or support arm articulation devices a common fasting element may be provided by means of which they are connected and/or the coupled with one another. The features and advantages resulting from the support arm articulation device according to the first aspect of the invention are detailed in the specification of the first aspect of the invention, wherein advantageous embodiments of the first aspect of the invention are to be regarded as advantageous embodiments of the second aspect of the invention and vice versa.

The support arm system may for example be formed as a ceiling supply unit, a wall support, monitor support, and/or is part of a movable solution. The support arm system may also comprise a base unit, as stationary fastening, one or more support arms which are connected to each other and/or at least one medical device which is held by means of the support arm system.

Preferably, the medical device is adjustably held at least by means of the support arm articulation device, in particular in the upward direction or in the vertical direction due to the pivot movement of the spring arm, in particular by pivoting the supporting arm in relation to the first and/or the second fastening element.

A third aspect of the invention relates to a method for operating a support arm articulation device and/or a support system according to the first or second aspect, wherein the adjustment device comprises at least the motor by means of which the position of the mounting of the lever arm on the supporting arm is adjustable. In addition, also the sensor device and the control device may be provided. The features and advantages resulting from the support arm articulation device according to the first aspect of the invention and the support arm system according to the second aspect of the invention are detailed in the specifications of the first and/or second aspect of the invention, wherein advantageous configurations of the first and second aspects of the invention are to be regarded as advantageous configurations of the third aspect of the invention and vice versa.

For operation, the support articulation device and/or the support arm system is provided, in particular including the medical device fastened thereon. In addition, a detection of a force acting on the support arm articulation device and/or a posture of the two fastening elements relative to each other is performed. Depending on the detected force acting on the support arm articulation device and/or the detected posture of the support arm articulation device, the motor of the support arm articulation device is controlled to maintain the relative posture of the two fastening elements motor relative to each other.

Thus for example, an application in the field of injectors may be enhanced. By emptying the fluid from the ejector, the appended load is reduced. Normally, a spring arm would thus no longer be in balance and move upwards. However, due to the adjustable spring arm, it is capable to maintain its position, thus a treatment of the patient may be performed.

Also an application in the field of a documentation terminal is very well feasible, in which a monitor and a keyboard are held, for example. When operating the keyboard, an additional operating force is introduced due to the entering operation, thus the spring arm might move downwards. This may also be compensated by the drive system.

Furthermore, the drive system also enables an exact positioning of a microscope, for example, which is controlled depending on a three-dimensional patient scan, for example.

Respective changes in weight force may be alternatively or in addition blocked by the adjustment mechanism, which for example prevents the displacement of the spring arm due to its friction in case of various small alterations in load.

Further features of the invention become apparent from the claims, the exemplary embodiments and the figures. The features and the combination of features mentioned in the specification above and the features and combinations of features mentioned in following exemplary embodiments may be used not only in the respective specified combination, but also in other combinations within the scope of the invention.

Here shows.

Figure 1:
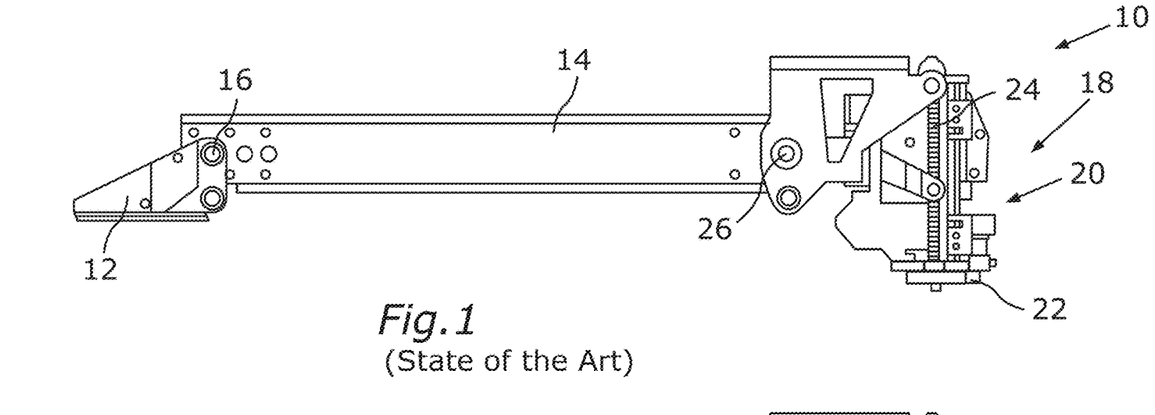
FIG. 1 in a schematic side view of a support arm articulation device according to prior art in a horizontal position.

FIG. 1 shows a schematic side view of a support arm articulation device according to prior art. This comprises a first fastening element 12 by means of which the support arm articulation device 10 may hold a surgical lamp, for example. On said fastening element 12 a support arm 14 is arranged. The support arm 14 is here connected to the first fastening element in a pivotable way by a pivot axis formed by the bolt 16. Further, the support arm articulation device 10 comprises a second fastening element 18 by means of which the support arm articulation device 10 may be fastened on a table, for example.

Figure 2:
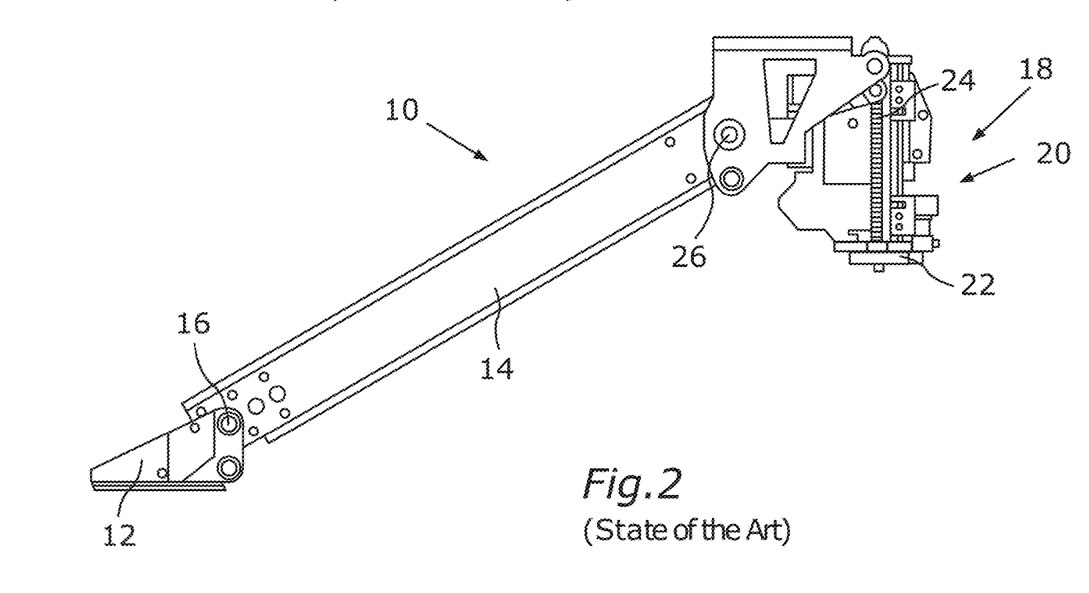
FIG. 2 in a schematic side view the support arm articulation device according to FIG. 1 in a lower position.

The second fastening element 18 comprises an adjustment device 20 which comprises a motor and a threaded spindle 24. Said adjustment device 20 is here connected to the support arm 40 like a rocker. Thereby, the support arm 14 may be pivoted upward and downward. A posture which is pivoted downward is shown in FIG. 2, for example, while FIG. 1 shows a horizontal posture. The pivot axis of the rocker is formed by an additional bearing pin 26.

As may immediately be seen in FIG. 1 and FIG. 2, a lever arm of the adjustment device 20 to the bearing pin 26 is significantly shorter than a lever arm from the first fastening element 12 to the bearing pin 26. Correspondingly, the surgery lamp being held on the first fastening element 12, for example, will create a substantially larger torque relative to the bearing pin 26 as a comparable force created by the adjustment device 20 due to the self-weight thereof. Correspondingly, the adjustment device 20 or the motor 22, respectively, has to be configured to be able to create a substantially larger force compared to the weight force to be held.

The design of the support arm articulation device 10 according to FIG. 1 and FIG. 2 thus requires a comparable strong and large motor 22. Such a design may for example be advantageous in case sufficient space is available, the motor 22 has to be very robust and a good accessibility for easy maintenance is required. The example shown is an adjustable support arm articulation device, the adjustment of which is performed by a direct force control.

However, especially in small places, for lightweight medical devices, and subtle surgeries, a simple precise adjustability of a support arm articulation device which at the same time has a small installation space and a simple design is advantageous, where appropriate.

Figure 3:
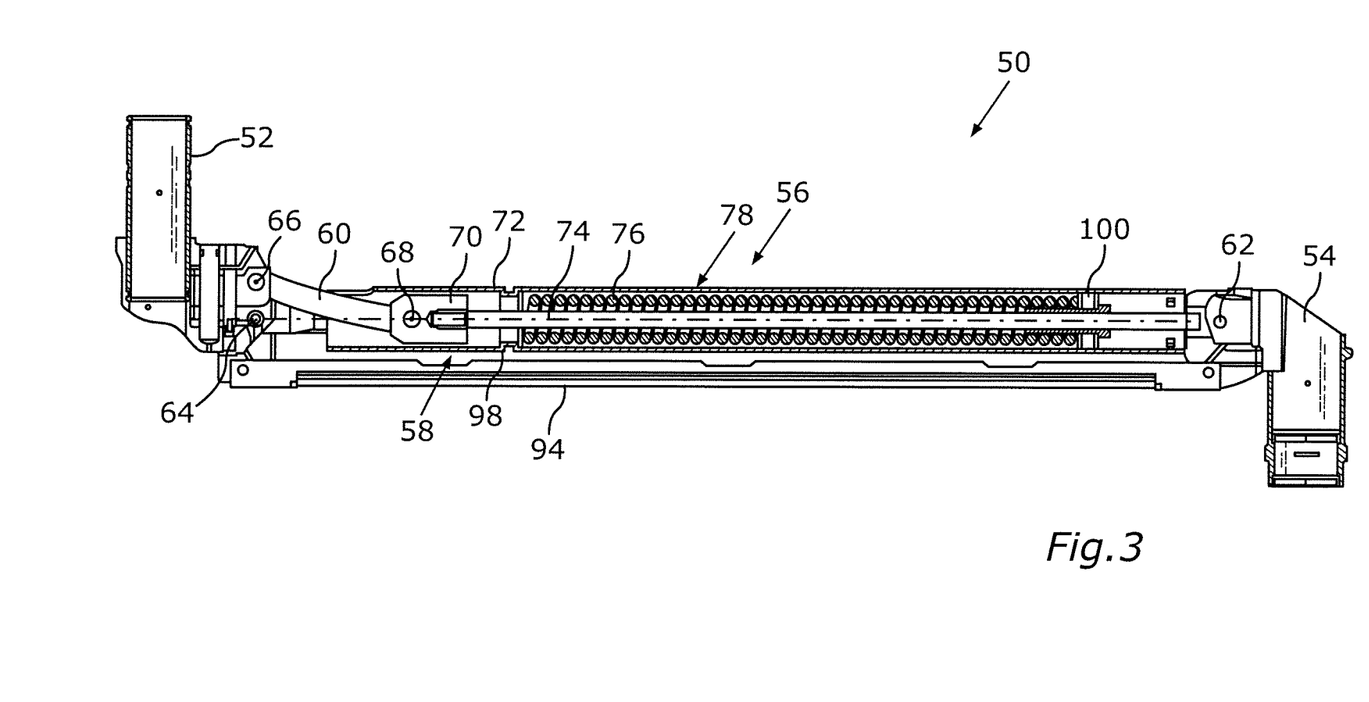
FIG. 3 in a symmetric side section view a support arm articulation device according to the invention in a horizontal position.

Thus, the support arm articulation device 50, as shown in a schematic side sectional view in FIG. 3, is provided which forms an articulated support arm. The support arm articulation device 50 comprises a first fastening element 52 by means of which the support arm articulation device 50 may be fastened on the ceiling of a surgery room, for example. Alternatively or in addition, the first fastening element 52 may also be arranged in a further support arm, for example. Further, the support arm articulation device 50 comprises a second fastening element 54, which is configured to fasten a medical device like a surgery lamp, or also a further support arm, for example. The two fastening elements 52, 54 are connected to each other by means of a spring arm 56, wherein the spring arm 56 enables a pivoting of the two fastening elements 52, 54 relative to each other. Herein the support arm articulation device 50 is configured in a way that pivoting is performed in a vertical plane, which herein equals the drawing plane of FIG. 3. Thus, the support arm articulation device 15 preferably enables the adjustment in height of a medical device held thereon.

Here, the spring arm 56 comprises a supporting arm 58 and a lever arm 60. The supporting arm 58 is here formed of several parts to which a tube 72 belongs, amongst others. The supporting arm 58 is here pivotably supported around a pivot axis on the first fastening element 52 at one end by means of a bolt 64. At an end facing away, the supporting arm 58 is also pivotally mounted on the second fastening element 54 by means of a further bolt 62. The extension from bolt 64 to bolt 62 corresponds to the axial extension of the supporting arm 58.

Herein, the lever arm 60 is formed as a rod and is mounted on the first fastening element 52 by means of a further bolt 66 so as to be pivotable at one end about its lever arm pivot axis. At the opposite end thereof, the lever arm 60 is also axially movably mounted in the tube 72 of the supporting arm 58 by means of a bolt 68 on a carriage 70. The carriage is held by a threaded rod 74, around which a coil spring 76 is arranged radially outward within the tube 72. The spring arm 56 thus has a spring device 78, by means of which respective weight forces acting on the support arm articulation device 50 may be supported.

As the lever arm 60 and the supporting arm 58 are mounted on the first fastening element 52 with their respective supporting arm pivot axis or lever arm pivot axis spaced apart from each other, a different lever arm or angle results depending on the posture of the support arm articulation device 50, by means of which the lever arm 60 supports the supporting arm 58. Thus, the same weight force may be consistently supported in different posture of the support arm articulation device 50. Therefore it is a well balanced spring arm 56.

Herein, the respective bolts 62, 64, 66, 68 are aligned parallel to one another. The respective bolts form an associated pivot axis, which extends perpendicular to the paper plane of FIG. 3. The respective bolts or the respective connections of parts may here thus also be denoted as axis or mounting.

Figure 4:
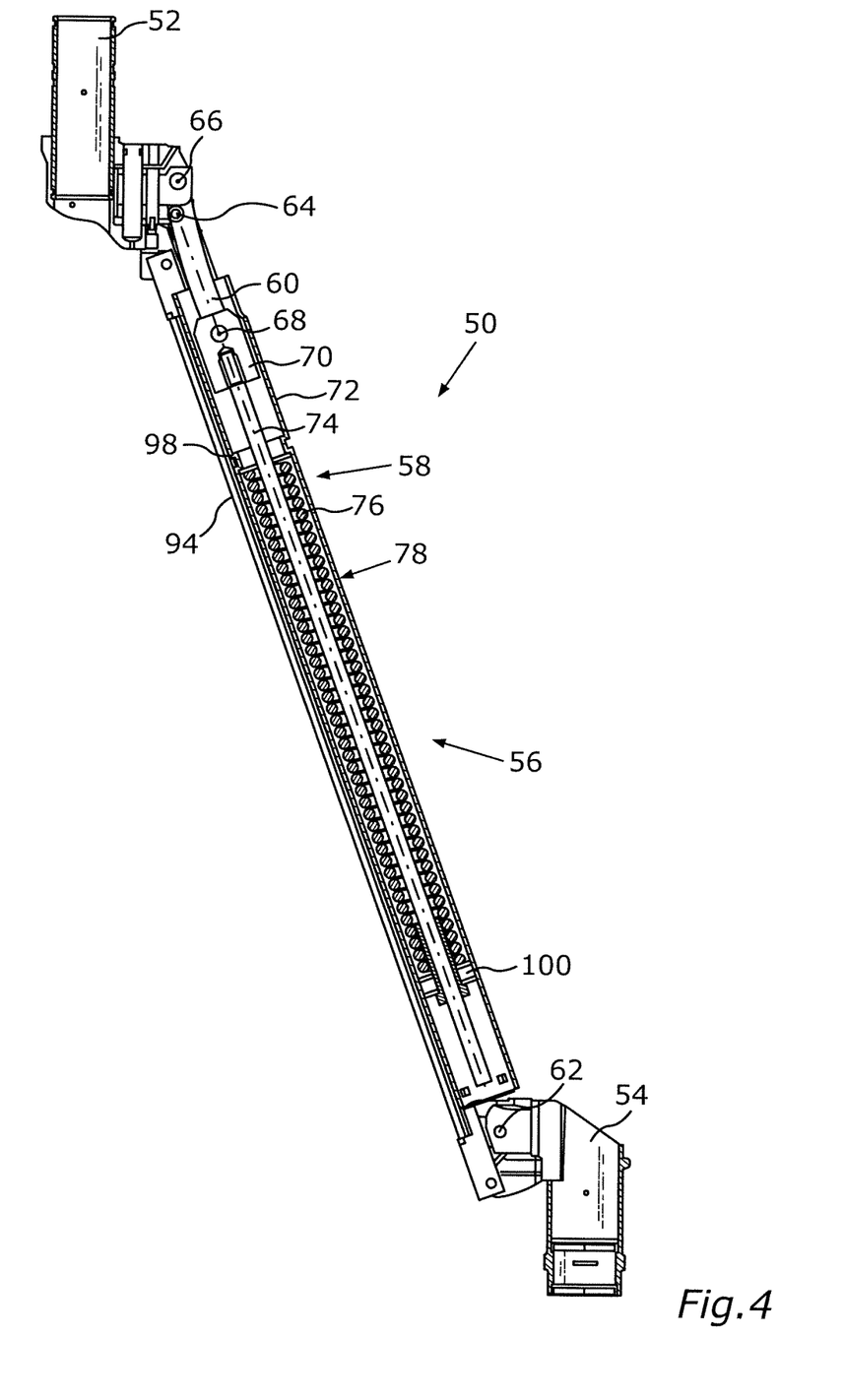
FIG. 4 in a schematic side section view the support arm articulation device according to FIG. 3 in a lower position.
Figure 5:
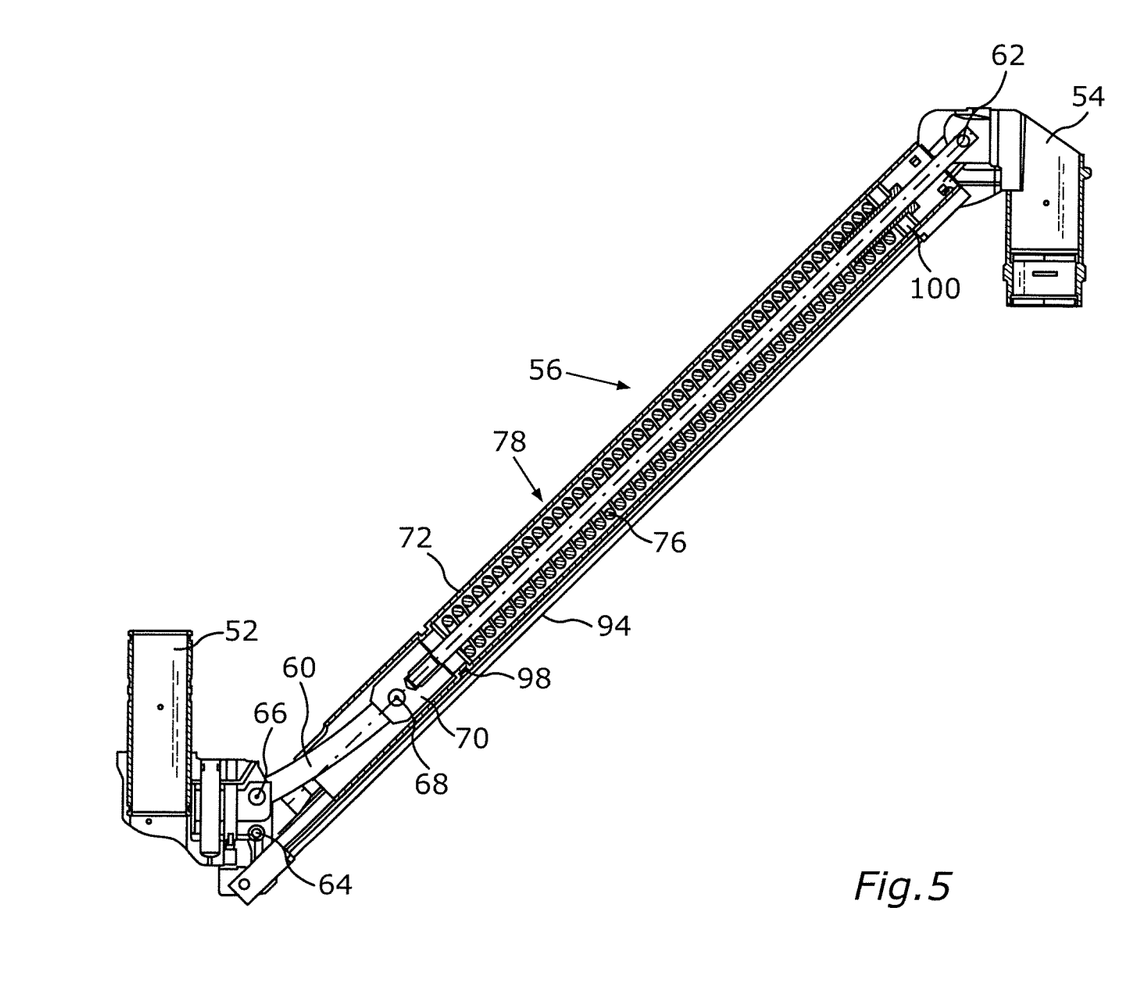
FIG. 5 in a schematic side section view the support arm articulation device according to FIG. 3 in an upper position.

FIG. 4 illustrates a lowermost position of the support arm articulation device 50, in which the spring arm 56 and/or the second fastening element 54, respectively, have been pivoted downwards as far as possible. In contrast, FIG. 5 shows an opposite top extreme position of the spring arm 56.

Respective directions of the acting forces and their respective associated lever arms for determining a torque acting due to this may thus easily be determined. FIG. 3 shows a substantially horizontal position of the support arm articulation device 50. Herein, the supporting arm 58 is pivoted against a horizontal position 70° downwards in FIGS. 4, and 45° upwards in FIG. 5.

Figure 7:
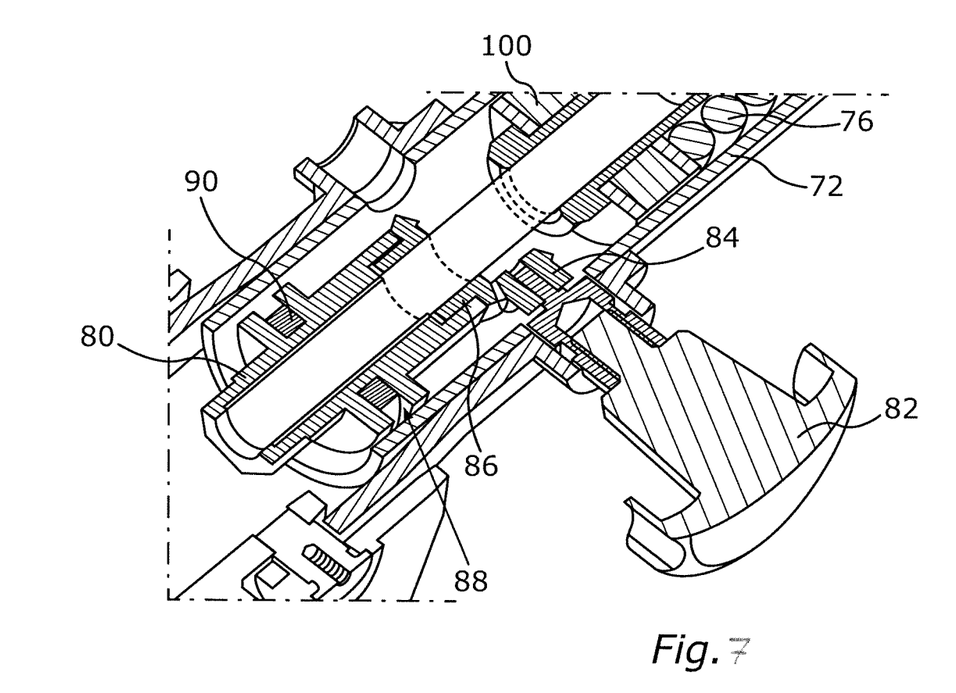
FIG. 7 the detail shown in FIG. 6 in a schematic perspective section view.
Figure 9:
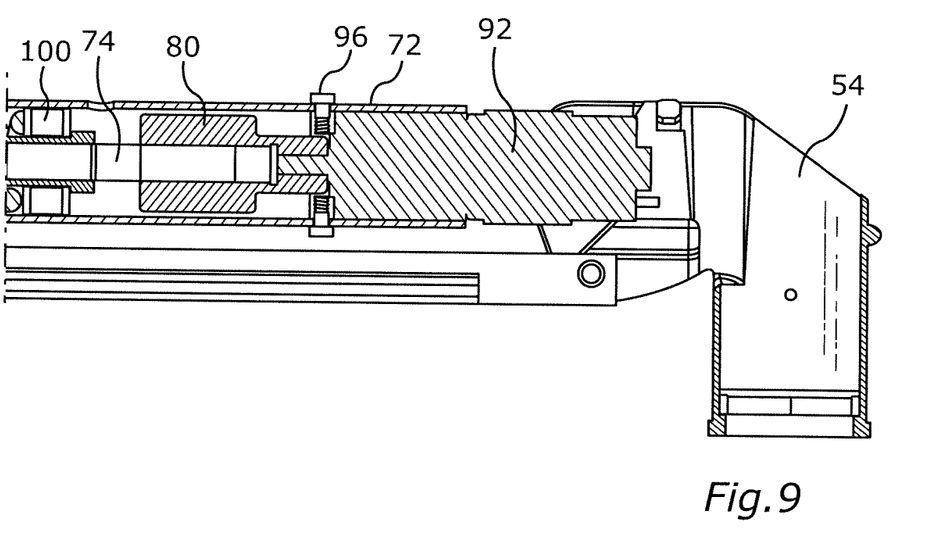
FIG. 9 the detail shown in FIG. 8 in a schematic side section view.

In the support arm articulation device 50, the posture or pivot angle thereof may be adjusted by adjusting the threaded rod 74 and thus axially moving the carriage 70 or a mounting of the lever arm 60 on the supporting arm 58 axially along the longitudinal extension of the supporting arm 58. Hereto, the threaded rod 74 is supported in the supporting arm 58 or the tube 72 by means of a nut 80 at the end facing away from the carriage 70. The nut 80 is shown in FIGS. 7 and 9, but not shown in FIGS. 3 to 5. Said nut 80 is thereby axially fixed to the supporting arm 58, but may be rotated about the longitudinal axis thereof in the circumferential direction. By rotating the nut 80, the threaded rod 74 is caused to move within the supporting arm 58 due to an engagement of the thread of the nut 80 and the threaded rod 74 with each other. For example, by moving to the right, as shown in FIG. 5, the carriage 70 is thus pulled in the corresponding direction by the coupled threaded rod 74, and the spring arm 56 is correspondingly adjusted upwards. In contrary, FIG. 4 shows a movement in the opposite direction, whereby the spring arm 56 is lowered downwards.

As may be seen in FIG. 4, a spring 76 of the spring device 78 is thus compressed in the position pivoted downwards. As a result, a potential energy released during lowering a device by the support arm articulation device 50 may be stored in the spring device 78. When the support arm articulation device is pivoted upward against the force of gravity, as shown in FIG. 5, the spring 76 is released, and releases thus the stored energy. This supports the pivoting movement or the adjustment of the carriage 70, respectively, thus the respective actuating forces may be particularly small during pivoting upwards. Similarly, a comparable large force may be required during lowering compared to pivoting upward, making adjustment intuitive and more precise in both directions. In FIGS. 3 to 5, gravity acts here downward in the image plane.

Preferably, the spring 76 is mounted in a prestressed way. In particular, the spring 76 may still have a pretensioning even in the uppermost position shown in FIG. 5 to enable a support over the entire adjustment range of the support arm articulation device 50. Herein, the spring 76 is formed as a pressure spring. Alternatively, the spring 76 may also be arranged in the axial direction of the supporting arm 58 on the side of the carriage 70 that faces the first attachment element 52 instead of the side that faces the second attachment element 54 in the axial direction. The spring 76 is supported on one side on an abutment 100, by means of which a spring force may be axially transferred to the threaded rod 74. At its opposite end, the spring 76 is axially supported on a tapering 98 of the tube 72. A washer is positioned on the tapering 98 to enhance mountability. The tapering 98 also limits a maximum axial movement of the carriage 70. Alternatively, the spring 76 may be supported directly on the carriage 70.

The adjustment device including the threaded rod 74 enables a particularly precise adjustment of the position of the support arm articulation device 50 due to the respective threads. In addition, the threaded rod 74 may provide a transmission ratio of an operating force, thus the support arm articulation device 50 may be moved or adjusted with little effort. In addition, the threaded rod 74 is self-blocking, i.e., in case of failure of a driving force, the support arm articulation device 50 does not lower itself automatically. In addition, load is taken off the adjustment device by the spiral spring 76, thus even lower operating forces are required. Low operating forces facilitate an adjustment and enable a more precise adjustment.

In the support arm articulation device 50, nearly all of the movable components of the supporting mechanism are almost completely accommodated within the tube 72 of the supporting arm 58, thus they are protected against environmental influences one the one hand and respective users are also protected from being crushed by moving parts. In addition, this enables a very compact and simple design, which may avoid in particular elaborate covers and housings.

Figure 6:
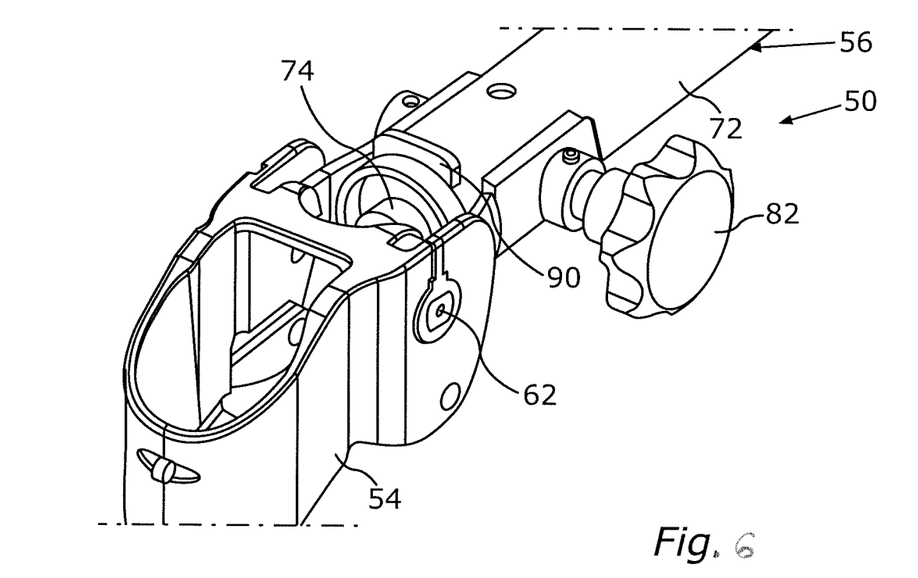
FIG. 6 in a schematic perspective view a detail of an embodiment of the support arm articulation device according to FIG. 3.

FIG. 6 and FIG. 7 illustrate a manually adjustable embodiment of the support arm articulation device 50 according to FIG. 3. As is shown, the support arm articulation device 50 according to FIG. 6 has a laterally arranged rotary button 82 as adjusting element. Said rotary knob 82 is connected by means of two bevel gears 84, 86 to the nut 80 to rotate it, which is formed herein as a spindle nut, for example. A nut 80 includes a groove 88, in which an abutment element 90 is arranged. By means of said abutment element 90, the nut 80 is axially fixed in the tube 72 but is rotatable in the circumferential direction thereof. For fixation, the abutment element 90 is guided through a through opening in the tube 72, as is shown in FIG. 6 and FIG. 7, respectively. This way, the support arm articulation device is easy to disassemble. By means of the respective bevel gears 84, 86, a further translation stage may be provided, which may either reduce the required operating force or may increase an adjustment speed. In addition, due to the respective bevel gears 84, 86, the rotary knob 82 may be arranged transversely to the longitudinal axis of the threaded rod 74, which enables a particularly compact design of the support arm articulation device 50.

Figure 8:
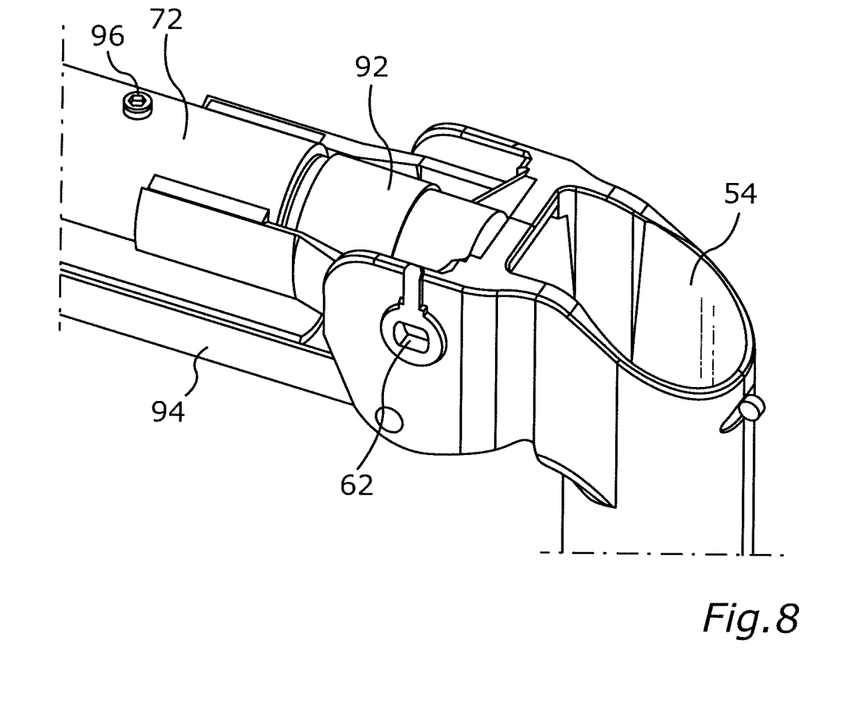
FIG. 8 in a schematic perspective view a detail of a further embodiment of the support arm articulation device according to FIG. 3.

On the other hand, FIG. 8 illustrates an embodiment of the support arm articulation device 50 according to FIG. 3, in which an adjustment is performed by means of a motor 92. This motor 92 is herein designed as an electric geared motor, which is arranged in an axial extension of the supporting arm 58. As shown in the section view according to FIG. 9, the motor 92 is attached to the tube 72 by means of corresponding clamping screws 94 and is clamped with the nut 80 and thus connected to the threaded rod 74 for a transfer of force. The nut 80 is also axially fixed, but rotatable in the circumferential direction. The nut 80 may be fixed correspondingly to the embodiment according to FIG. 6, or may also be fixed to the motor 92, for example. Alternatively, however, the motor 92 may be directly connected to the threaded rod 74 for adjustment or rotation thereof. As shown in FIG. 9, the motor 92 may also be at least partially disposed within the tube 72, as it needs to provide only little torque and little power due to the design of the support arm articulation device 50. This way, the support arm articulation device 50 may be especially compact and simple.

In addition, it is shown in FIGS. 3 to 5, FIG. 8, and FIG. 9 that the support arm articulation device 50 may include a parallel guiding member 94. Herein, the parallel guiding element 94 is formed as a rod which is pivotably mounted on the first fastening element 52 with a first end and pivotably mounted on the second fastening element 54 with a second end. The parallel guiding element 94 synchronizes a pitch movement of the two fastening elements 52, 54 with a pivoting movement of the spring arm 56. This way, an alignment of the two fastening elements 52, 54 may remain the same for any positions of the spring arm 56. This may be determined directly by comparing FIG. 3, FIG. 4, and FIG. 5 with each other, in which the orientation of the two fastening elements 52, 54 in the image or drawing plane remains the same.

LIST OF REFERENCE NUMBERS

10 Support arm articulation device
12 First fastening element
14 Support arm
16 Bolt
18 Second fastening element
20 Adjustment device
22 Motor
24 Threaded spindle
26 Bearing pin
50 Support arm articulation device
52 First fastening element
54 Second fastening element
56 Spring arm
58 Supporting arm
60 Lever arm
62 Bolt
64 Bolt (supporting arm pivot axis)
66 Bolt (lever arm pivot axis)
68 Bolt (axis of rotation)
70 Carriage
72 Tube
74 Threaded rod
76 (coil) spring
78 Spring device
80 Nut
82 Rotary knob (Adjusting element)
84 Bevel gear
86 Bevel gear
88 Groove
90 Abutment element
92 Motor
94 Parallel guiding element
96 Clamping screw
98 Tapering
100 Abutment

The invention claimed is:

1. A support arm articulation device (50) for a support system for movably holding at least one medical device, comprising
a first and a second fastening element (52, 54), which are connected to each other by means of a spring arm (56) in a pivotable way relative to each other, and
wherein the spring arm (56) comprises a supporting arm (58) and a lever arm (60), which are mounted in a pivotable way on the first fastening element (52) with an associated supporting arm pivot axis (64) and lever arm pivot axis (66),
wherein the two pivot axes (64, 66) are spaced apart from each other,
wherein the supporting arm (58) is mounted on the second fastening element (54) in a pivotable way, and the lever arm (60) is mounted on the supporting arm (58) by means of a spring device (78) such that a weight force of the held medical device is supported in different pivot positions,
wherein the spring device (78) comprises an adjustment device by means of which a position of the mounting (68, 70) of the lever arm (60) on the supporting arm (58) is adjustable along a longitudinal extension of the supporting arm (58) and wherein the adjustment device comprises an adjusting element (82) configured to precisely adjust the held medical device in a vertical plane,
wherein the supporting arm (58) includes a tube (72) and the adjusting element (82) is a rotary knob.

2. The support arm articulation device (50) according to claim 1, wherein the spring device (78) comprises a spring (76) which is preferably guided essentially within the supporting arm (58).

3. The support arm articulation device (50) according to claim 1, wherein the lever arm (60) is mounted on the spring device (78) in a pivotable way, in particular with a pivot axis (68) parallel to the lever arm pivot axis (66) by means of which the lever arm is mounted on the first fastening element (52).

4. The support arm articulation device (50) according to claim 1, wherein the lever arm (60) is mounted on the supporting arm (58) along the longitudinal extension thereof by means of a carriage (70), wherein the carriage (70) is preferably guided essentially inside the supporting arm (58).

5. The support arm articulation device (50) according to claim 1, wherein the adjustment device comprises a threaded rod (74) connected to the adjusting element (82), wherein by movement thereof, the position of the mounting (68, 70) of the lever arm (60) on the supporting arm (58) can be adjusted.

6. The support arm articulation device (50) according to claim 5, wherein the threaded rod (74) is mounted on an axially fixed and rotatable nut (80) which is fastened in or to the supporting arm (58).

7. The support arm articulation device (50) according to claim 6, wherein the threaded rod (74) is at least partially arranged within the supporting arm (58).

8. The support arm articulation device (50) according to claim 7, wherein the threaded rod (74) is partially arranged within the supporting arm (58) in one posture or position and completely arranged within the supporting arm (58) in another posture or position.

9. The support arm articulation device (50) according to claim 1, wherein the adjusting element (82), by means of which the position of the mounting (68, 70) of the lever arm (60) on the supporting arm (58) is adjustable is mounted on the supporting arm (58).

10. The support arm articulation device (50) according to claim 1, wherein the support arm articulation device (50) comprises a parallel guiding element (94), which is pivotably mounted on the first fastening element (52) and the second fastening element (54), respectively, at a distance from the supporting arm (58).

11. The support arm articulation device (50) according to claim 10, wherein the respective mounting axes of the parallel guiding element (94) are parallel to one another and/or to the respective mounting axes of the supporting arm (58).

12. The support arm articulation device (50) according to claim 1, wherein the support arm articulation device (50) is configured to adjust a supporting force to different weight forces of different held medical devices in different pivot positions, in particular by replacing the spring (76) of the spring device (78), adjusting a prestressing force of the spring device (78) and/or adjusting a distance between the lever arm pivot axis (66) and the supporting arm pivot axis (64) on the first fastening element (52).

13. The support arm articulation device (50) according to claim 1, wherein the first fastening element (52) and/or the second fastening element (54) is/are configured for fastening to a wall, a ceiling, a floor, a movable and/or a stationary base unit, and/or
wherein the first fastening element (52) and/or the second fastening element (54) is/are configured for coupling to a support arm, a joint, a further support arm articulation device (50) and/or the or a medical device.

14. A support arm system for movably holding at least one medical device comprising at least one support arm articulation device (50) according to claim 1.

15. The support arm system according to claim 14, wherein the support arm system comprises one or more support arms (14) coupled to the support arm articulation device (50).

16. A method for operating a support arm articulation device (50) according to claim 1, comprising at least the following steps:
providing the support arm articulation device (50) with the medical device fastened thereto;
detecting a force acting on the support arm articulation device (50) and/or a posture of the two fastening elements (52, 54) relative to each other; and
controlling the motor (92) of the support arm articulation device (50) depending on the detected force acting on the support arm articulation device (50) and/or the detected posture of the support arm articulation device for maintaining the posture of the two fastening elements (52, 54) relative to each other.

17. The support arm articulation device (50) according to claim 1, wherein the rotary knob is connected by two bevel gears (84, 86) to a nut (80) to rotate the rotary knob, wherein the nut (80) includes a groove (88), in which an abutment element 90 is arranged, and wherein the nut (80) is axially fixed in the tube (72), but is rotatable in a circumferential direction thereof.

18. A support arm articulation device (50) for a support system for movably holding at least one medical device, comprising
a first and a second fastening element (52, 54), which are connected to each other by means of a spring arm (56) in a pivotable way relative to each other, and
wherein the spring arm (56) comprises a supporting arm (58) and a lever arm (60), which are mounted in a pivotable way on the first fastening element (52) with an associated supporting arm pivot axis (64) and lever arm pivot axis (66),
wherein the two pivot axes (64, 66) are spaced apart from each other,
wherein the supporting arm (58) is mounted on the second fastening element (54) in a pivotable way, and the lever arm (60) is mounted on the supporting arm (58) by means of a spring device (78) such that a weight force of the held medical device is supported in different pivot positions, wherein the spring device (78) comprises an adjustment device by means of which a position of the mounting (68, 70) of the lever arm (60) on the supporting arm (58) is adjustable along a longitudinal extension of the supporting arm (58), and wherein the adjustment device comprises a threaded rod (74) connected to a motor (92) configured to precisely adjust the held medical device in a vertical plane, wherein the supporting arm (58) includes a tube (72) and the motor (92) is attached to the tube.

19. The support arm articulation device (50) according to claim 18, wherein the motor (92) is attached to the tube (72) by means of corresponding clamping screws (94) and is clamped with a nut (80) and thus connected to the threaded rod (74) for a transfer of force.

20. The support arm articulation device (50) according to claim 18, wherein the support arm articulation device (50) comprises a sensor device, which is configured to detect a force acting on the support arm articulation device (50) and/or a posture of the two fastening elements (52, 54) relative to each other, and wherein the support arm articulation device (50) comprises a control device which, depending on the detected force acting on the support arm articulation device (50) and/or the detected posture of the support arm articulation device (50), controls the motor (92) to maintain the relative posture of the two fastening elements (52, 54) relative to each other.

* * * * *